(12) United States Patent
Wang (10) Patent No.: US 7,558,365 B2
(45) Date of Patent: Jul. 7, 2009

(54) SCANNING DETECTION DEVICE OF AN X-RAY CT APPARATUS, AN X-RAY CT SYSTEM, AND METHOD OF OPERATION OF THE SAME

(75) Inventor: Xueli Wang, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 12/143,569

(22) Filed: Jun. 20, 2008

(65) Prior Publication Data
US 2009/0016484 A1 Jan. 15, 2009

(30) Foreign Application Priority Data
Jun. 22, 2007 (CN) .......................... 200710126224

(51) Int. Cl.
*G01N 23/00* (2006.01)
(52) U.S. Cl. ............................ 378/16; 378/4
(58) Field of Classification Search ...................... 378/5, 378/4, 8, 16, 19–20, 13, 15
See application file for complete search history.

(56) References Cited

U.S. PATENT DOCUMENTS

| 5,379,333 | A | 1/1995 | Toth |
| 5,400,378 | A | 3/1995 | Toth |
| 5,485,494 | A | 1/1996 | Williams et al. |
| 5,696,807 | A | 12/1997 | Hsieh |
| 5,822,393 | A | 10/1998 | Popescu |
| 6,285,741 | B1 | 9/2001 | Ackelsberg et al. |
| 6,904,127 | B2 | 6/2005 | Toth et al. |
| 7,050,532 | B2 | 5/2006 | Gohno |
| 2006/0115039 | A1* | 6/2006 | Gohno .......................... 378/4 |
| 2006/0285634 | A1* | 12/2006 | Toth ............................ 378/16 |
| 2007/0071160 | A1 | 3/2007 | Nishide et al. |
| 2007/0076842 | A1* | 4/2007 | Tkaczyk et al. ................ 378/5 |
| 2007/0258559 | A1 | 11/2007 | Hur |

* cited by examiner

*Primary Examiner*—Hoon Song
(74) *Attorney, Agent, or Firm*—Armstrong Teasdale LLP (57) ABSTRACT

Method of operating an X-ray CT apparatus and the corresponding apparatus and system thereof. A method includes analyzing scout scan data to obtain a position with a minimum noise index and a position with a maximum noise index, calculating noise indexes at the two positions in a range of a maximum and a minimum tube current that can be provided by the system by means of a tube current control model so as to obtain two ranges of noise index, and determining whether there is an intersection between the two ranges of noise index. If such an intersection exists, a combination of the range of tube current value and the range of noise index that meets the requirement is selected within the intersection to control the system to proceed with a subsequent scan. If no such intersection exists, the system ends the present scan.

20 Claims, 10 Drawing Sheets

| Add Group | Split | Delete Group | Puncture | Smart Tracking | Browse mA List | No Optimize | Gating Cardiograph | ◁ Backward | ▷ Forward |
|---|---|---|---|---|---|---|---|---|---|
| Image Num | Scan Type | Start | End | Image Num | Thickness (mm) | Interval (mm) | Gantry Tilt | SFOV | kV | mA | Scan Time (sec) |

| 1-108 | Axial Full 2.0 sec. | S149.250 | I118.500 | 108 | 2.5 4i | 10.000 | S0.0 | Large | 1.40 | 15 1.00 | 54.0 |

| End Exam | Select Protocol | Next Series | New Series | Repeat Series | Add Scan | Prior Recon | Auto Scan | Confirm |

SCANNING DETECTION DEVICE OF AN X-RAY CT APPARATUS, AN X-RAY CT SYSTEM, AND METHOD OF OPERATION OF THE SAME

CROSS REFERENCE TO RELATED APPLICATIONS

This application claims the benefit of Chinese Patent Application No. 200710126224.7 filed Jun. 22, 2007, which is hereby incorporated by reference in its entirety.

BACKGROUND OF THE INVENTION

The subject matter disclosed herein relates to an operation method of an X-ray CT apparatus and an X-ray CT (Computed Tomography) apparatus, in particular to a method for detecting whether an X-ray CT apparatus can meet the requirement for scanning an object to be scanned and the CT apparatus and system using said detection method.

X-ray is known to be harmful to the tissues and organs of human body, so the manufacturers of X-ray CT apparatuses try their best to make the X-ray CT apparatuses they manufactured obtain better scan images with the lowest X-ray radiation amount as it can be. Thus an intelligent tube current control model has been invented and applied to X-ray CT apparatuses, which can ensure a uniform noise value among the scan images of all the cross sections obtained by using tube current of different magnitudes to each of the scanned cross sections. Currently, the tube current control model has been widely used in the field of CT apparatus and has become a very important characteristic of the CT apparatus and system.

Figure 1:
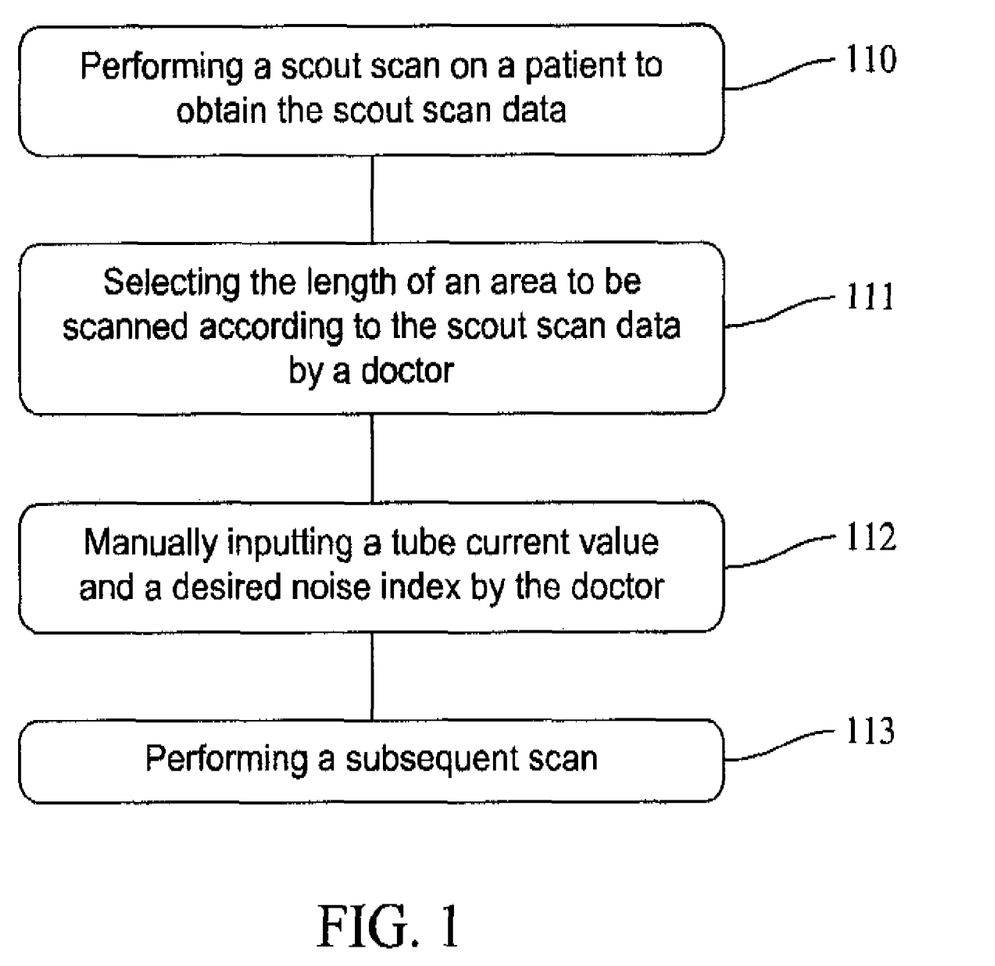
FIG. 1 shows the scanning method of the existing CT apparatus.
Figure 2:
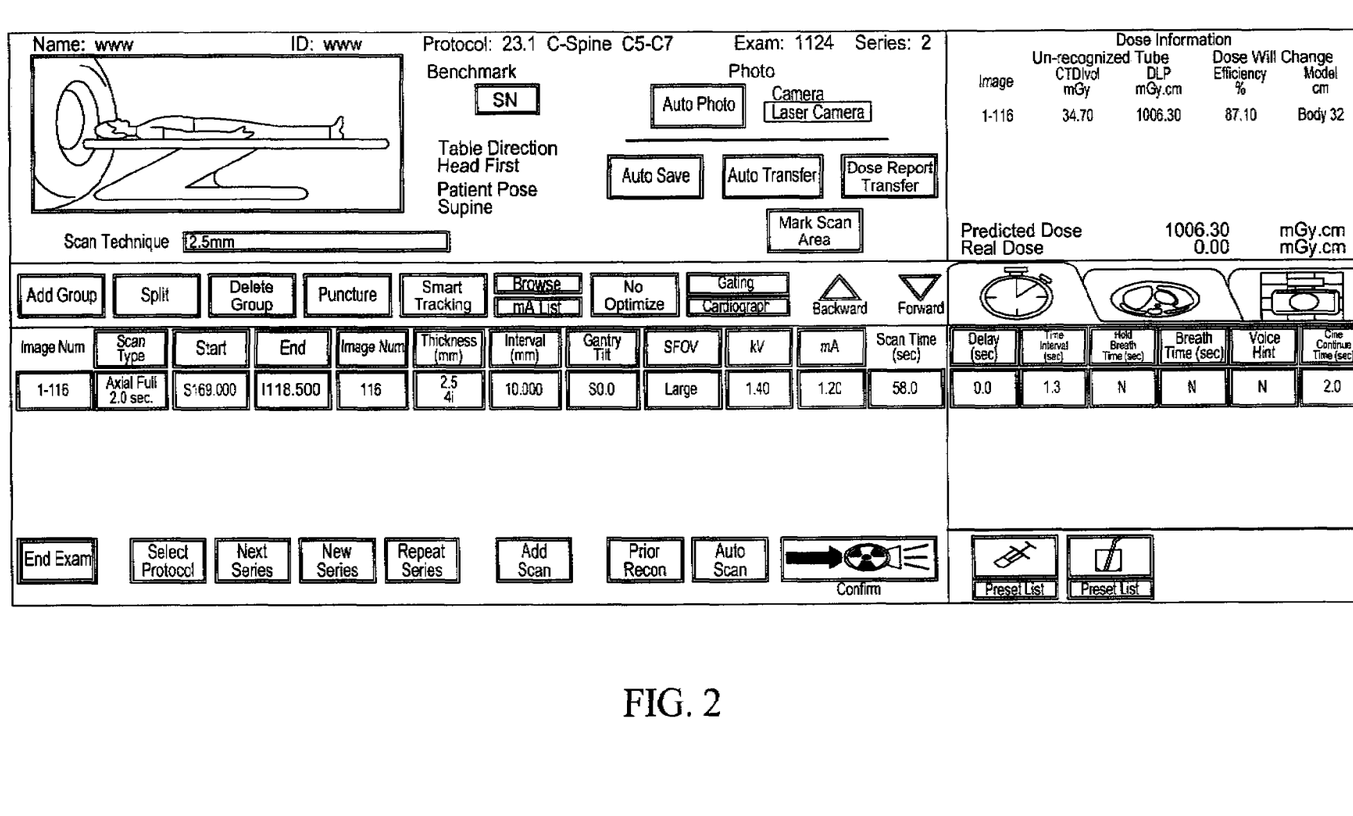
FIG. 2 is the operation interface of the existing scanning apparatus of FIG. 1 for the user's scanning operation.
Figure 3:
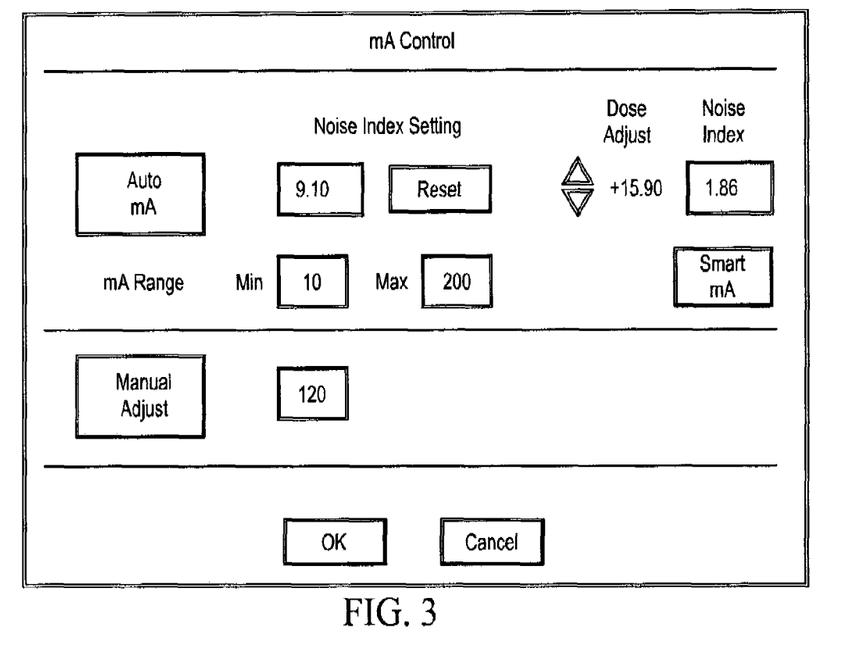
FIG. 3 is a tube current control interface of the existing scanning apparatus of FIGS. 1 and 2.
Figure 4:
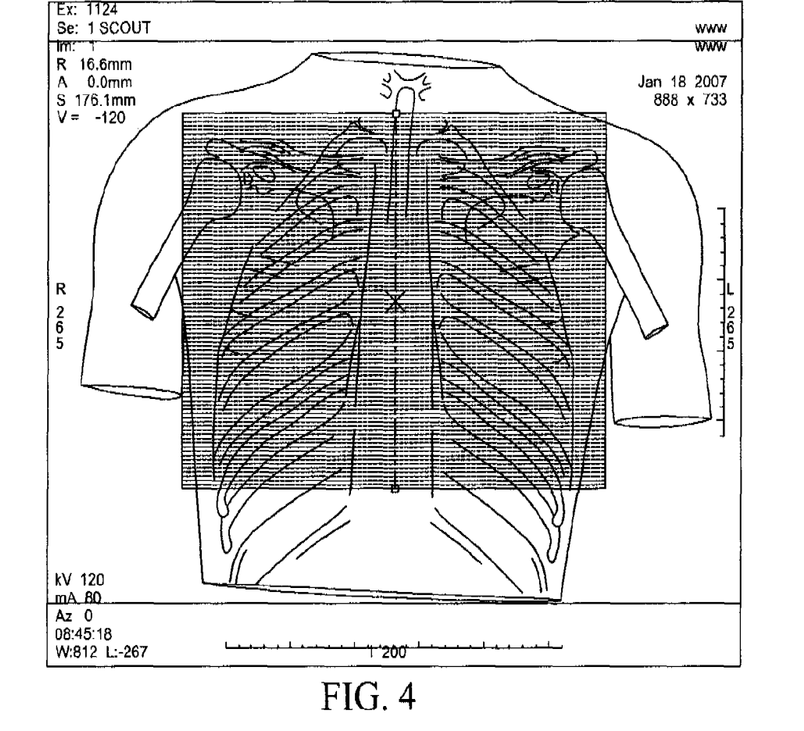
FIG. 4 is the scout scan image obtained by means of the method of FIG. 1.

For an existing CT apparatus having a tube current control model, the flow of executing a scan is as shown in FIG. 1, wherein a scout scan is performed on a patient in step 110 to obtain the scout scan data; in step 111 a doctor chooses the length of an area to be scanned according to the scout scan data; step 112 is that the doctor manually input the range of tube current value and the desired noise index after determining the range of the length of the area to be scanned; then in step 113, the CT apparatus performs the subsequent scanning according to the tube current and the noise index set by the doctor. Correspondingly, the operation interface of the CT apparatus having a tube current control model is as shown in FIGS. 2 and 3, and the operation mode thereof is as the following: the patient is sent into CT to be scanned, a scout scan is performed on the patient, and a scout scan image is obtained, as shown in FIG. 4. Then the tube current button on the user operation interface as shown in FIG. 2 is pressed to activate the tube current control box as shown in FIG. 3 to pop up a user operation interface for tube current control; proper noise index and range of tube current value are entered in the tube current control in FIG. 3 according to the data of the scout scan image, the button of "Confirm" in FIG. 3 and then the button of "Confirm" in FIG. 2 are pressed to perform the subsequent scanning.

However, the existing CT apparatus having a tube current control model have the following disadvantages:

First, if the doctor is not clear about the setting of the noise index of the operated CT apparatus, then when the doctor sets a noise index to scan the patient, the noise index of the resulted scan image is quite different from the value set by the user. This makes the doctor doubt the result of examination and even re-scan the patient, thus making the patient suffer from more X-ray radiation.

Second, when testing the function of the apparatus, failure of test sometimes occurs. After resetting the range of tube current and noise index in the corresponding positions as shown in FIG. 3, the previously failed testing item may pass smoothly. But sometimes, even if the range of tube current value and/or index are reset, the test still fails, thus the tester may become confused and wonder what on earth the appropriate range of test value should be.

Figure 5:
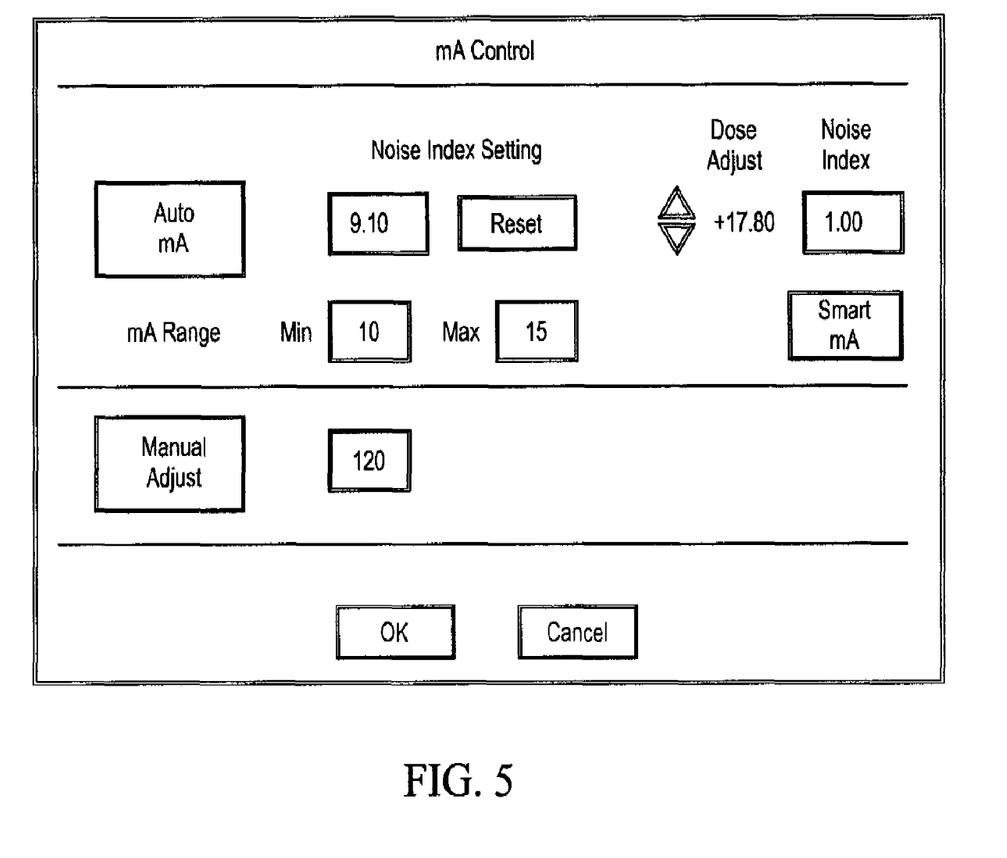
FIG. 5 is another tube current control interface of the existing scanning apparatus shown in FIGS. 1 and 2.

Third, the noise index and the range of tube current value are independent from each other in the tube current control parameter input user operation interface of the existing CT system, as shown in FIG. 5. Therefore, in this tube current control interface, the input of the range of tube current value does not influence the input of the noise index, and vice versa.

Figure 6:
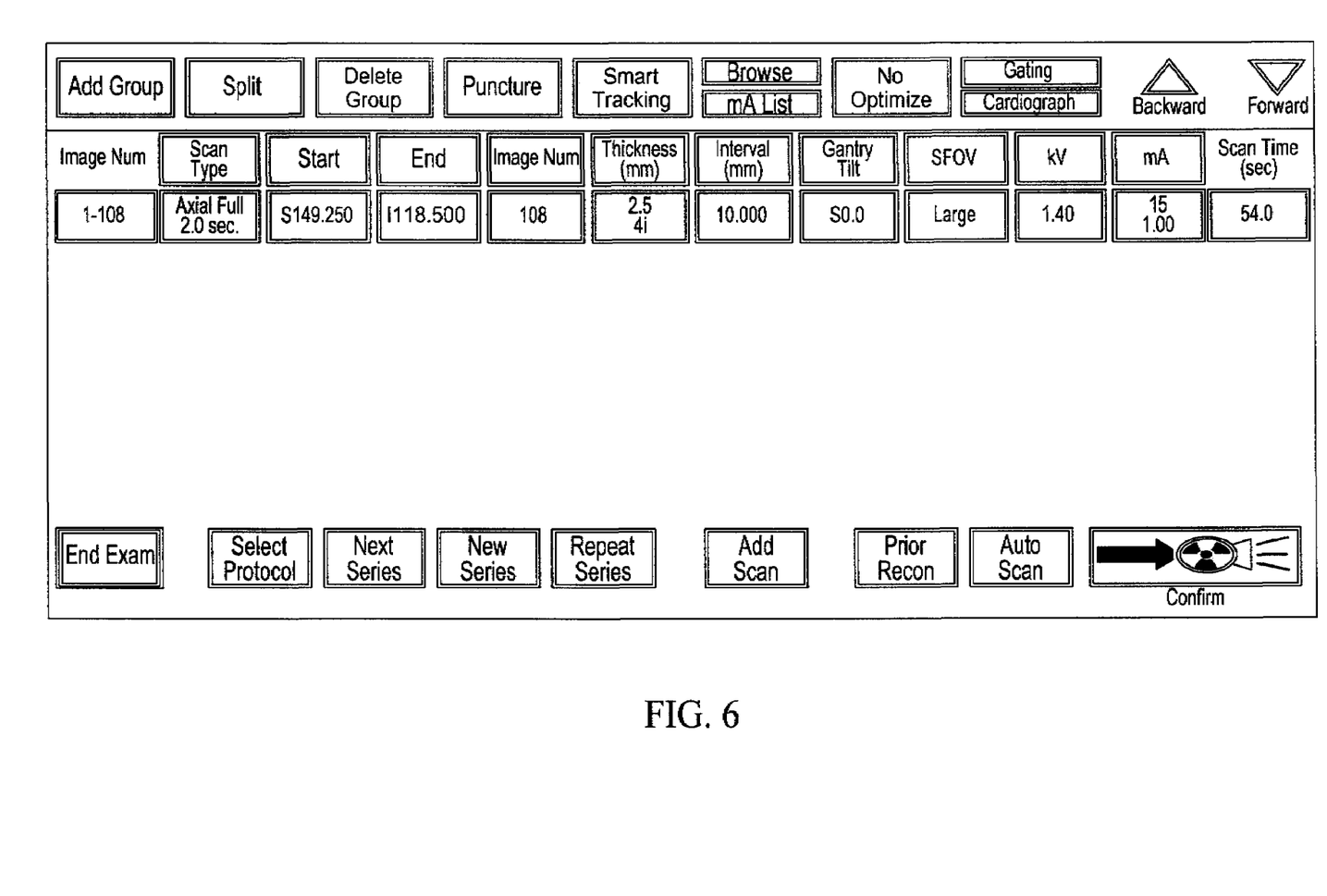
FIG. 6 is a known user operation interlace for special parameter setting.

Take the parameters as shown in FIG. 5 as an example, if the noise index is set to be 1.0, and the maximum tube current value is set to be 15 mA at the same time, then the whole scan can be carried out smoothly, as shown in FIG. 6. A phantom of a scanned object is extracted under such set parameters, and in the output image, it can be seen that the maximum tube current value is lower than 15 mA; obviously, a image with a noise index of 1.0 cannot be obtained. However, in the output image, we do see the characteristic of the noise index being 1.0. Such serious mismatch makes the scan image in a mess and with a lot of noise, as a result, it might be necessary to re-scan the patient, thereby making the patient suffer from more X-ray radiation.

Likewise, if the preset minimum value in the range of tube current value is comparatively large, for example, 200 mA, and for some patients, the doctor sets and inputs a noise index of 15, but in fact, it is possible that some tomographic images of the patient can reach the noise index of 15 only with a current of 150 mA, while unfortunately, the minimum value that is available in the system is 200 mA. Therefore, in the output scan image, the actual minimum tube current value is 200 mA, while the noise index is still shown to be 15. The noise index of such output image is not consistent with the actual noise index, which also makes the patient suffer from unnecessary radiation dosage.

In summary, in the existing X-ray CT apparatus having a tube current control model, since its two parameters, namely, the tube current value and the noise index are independent from each other, the setting and input of one parameter will not cause the input of the other parameter. Thus during operation, when the user inputs one parameter, the system cannot automatically display the range of the other parameter matching said input parameter. And the user has to set the other parameter according to his experience, and this may result in a great difference between the output scan image and the set parameters. Accordingly, the condition of the patient cannot be truly reflected or the patient is made to accept too much radiation. In addition, such X-ray CT apparatus having the tube current value and the noise index set independently makes the doctor blindly scans an object to be scanned without knowing whether said system has the scanning condition for the object to be scanned in which the requirements for the tube current value and the noise index are both met.

BRIEF DESCRIPTION OF THE INVENTION

Described herein are a method for operating an X-ray CT apparatus and the apparatus itself for solving the above-mentioned problem. More specifically, the embodiments herein provide a method and an apparatus for effectively combining the tube current value parameter, the noise index parameter and the scout scan image, which has good judgment, high image quality, and low radiation amount.

In one aspect, a method of operating an X-ray CT apparatus includes performing a scout scan on a subject to obtain scout scan data, selecting the length of an area to be scanned according to the scout scan data, and automatically analyzing in the length of the area to be scanned by means of a tube current control model, and calculating the noise index of each Z-direction position under a certain fixed tube current value to select the position with the maximum noise index value and the position with the minimum noise index value. The method also includes substituting the maximum and minimum tube current values that can be provided by the present scan of the system respectively into the existing tube current control model of the system so as to calculate the range of noise index of the position with the minimum noise index in the scanned area and the range of noise index of the position with the maximum noise index in the scanned area, and determining if there is an intersection between said two ranges of noise index. If such an intersection exists, the method includes selecting within the intersection a combination of the range of tube current value and the range of noise index that meets the requirement to perform a subsequent scan. If such an intersection does not exist, it means that the system does not meet the requirement for the area to be scanned and the present scan is ended.

In one embodiment, selecting a combination of the range of tube current value and the range of noise index includes creating a combination wherein the respective ranges of tube current value and the noise index that meet the requirement are of a one-to-one correspondence relationship.

The number of said combinations is obtained by equally dividing the range of noise index in the intersection according to a value of the dosage adjustment range of the noise coefficient.

In the method of the present invention, the correspondence relationship between the range of tube current value and the noise index that meet the requirement by means of a graph.

The graph is a graph of a combination of the ranges of tube current value corresponding to the respective ranges of noise index that meet the requirement, and the horizontal axis thereof represents the noise index and the longitudinal axis thereof represents the range of tube current value. In one embodiment, the graph is a histogram.

In another embodiment, the graph is a graph of a combination of the maximum and minimum tube current values corresponding to the respective noise indexes that meet the requirement, and the horizontal axis thereof represents the maximum tube current value and the longitudinal axis thereof represents the minimum tube current value. In such an embodiment, the graph is a block diagram, and the minimum tube current value is equal to or less than the maximum tube current value.

The maximum and minimum tube current values that can be provided by the system are determined through the information of the present scout scan image and technical parameters of the present scout scan including the voltage value and the thickness.

After selecting a combination of the range of tube current value and the range of noise index that meets the requirement, the maximum value and minimum value in the range of tube current value in the combination are automatically loaded into the block of the range of tube current value in the tube current control interface of the system, and the corresponding noise index is also loaded into the block of the noise index in the tube current control interface of the system. The noise value can be adjusted within the range of noise index.

In another aspect, a scanning detection device is provided for an X-ray CT system having a tube current control model, wherein the X-ray CT system having a tube current control model comprises a scanning gantry for performing a radiation scan including a scout scan on a subject, a data processing unit for collecting and processing the scout scan data output from the scanning gantry, an image reconstruction unit for reconstructing image according to the scout scan data sent from the data processing unit, a central control unit for controlling the whole system, and a user operation interface for a user to operate. The user selects the length of an area to be scanned according to the scout scan data and the scout scan image. The scanning detection device comprises a unit for determining a position of a certain noise index value, which applies the tube current control model to the length of the area to be scanned to find out the first position with the minimum noise index and the second position with the maximum noise index in the Z-direction of the length of the area to be scanned; a unit for determining the range of tube current value of the system, which determines the maximum and minimum tube current values that can be provided by the present scan according to the scout scan data output from the scanning gantry and system technical parameters of the present scan; a calculating unit which substitutes the maximum and minimum tube current values that can be provided by the system into the tube current control model in the system to calculate the range of noise index of the first and second positions that are found out by the unit for determining a position of a certain noise index value; and a determining unit which determines if there is an intersection between the two ranges of noise index calculated by the calculating unit, if there is, a message indicating a subsequent scan is to be performed is displayed on the user operation interface, the value of the range of noise index within the intersection and the corresponding ranges of the maximum and minimum tube current values are used as parameters for a subsequent scan; if there is not, an message indicating the present scan is to be ended is displayed through the user operation interface.

In one embodiment, the device includes a data combining unit which combines and divides data including the range of tube current value and the range of noise index within the intersection to establish a relationship of one-to-one correspondence.

The central control unit performs graphical processing on the correspondence relationship established by the data combining unit and displays it on the user operation interface in a graph.

In one embodiment, the graph is a graph of a combination of the ranges of tube current value corresponding to the respective ranges of noise index that meet the requirement, and the horizontal axis thereof is the noise index and the longitudinal axis thereof is the range of tube current value.

In another embodiment, the graph is a graph of a combination of the maximum and minimum tube current values corresponding to the respective noise indexes that meet the requirement, and the horizontal axis thereof is the maximum tube current value and the longitudinal axis thereof is the minimum tube current value.

The number of said data combinations is obtained by equally dividing the range of noise index in the intersection according to a value of the dosage adjustment range of the noise coefficient provided by the system.

The user operation interface includes a tube current control interface, and said graph and the tube current control interface are in the same user operation interface. When an operator clicks on any position on the graph, the user operation interface will automatically pop up the value of the range of noise index and the range of tube current value of the combination represented by said position.

An automatic filling relationship is established between said graph and tube current control interface. When the operator clicks on any position on the graph, the value of the range of noise index and the range of tube current value of the combination represented by said position will be automatically filled into the box for the range of tube current value and the box for the noise index in the tube current control interface.

Said system technical parameters include parameters of voltage value and thickness.

In another aspect, an X-ray CT system having a tube current control model for processing scan data is provided, which comprises: a scanning gantry for performing a radiation scan including a scout scan on a subject; a data collecting unit for collecting and A/D converting the scan data including the scout scan data output from the scanning gantry; an image reconstruction unit for reconstructing a image from the scan data including the scout scan data sent from the data collecting unit, and for storing data of the reconstructed scout scan image in a storage unit; a user operation interface for a user to operate, through which the user selects the length of an area to be scanned according to the scout scan data and the scout scan image; and a central control unit connected to an output of the image reconstruction unit for controlling the scanning gantry, the data collecting unit and the user operation interface. The central control unit receives an operation instruction of selecting the length of the area to be scanned as sent from the user operation interface, selects the length of the area of the scout scan image sent from the image reconstruction unit, and displays it on the user operation interface. The central control unit comprises a position determining unit which performs analysis in the length of the area to be scanned by means of the tube current control model and calculates the noise index of each Z-direction position at a certain fixed tube current value to find out the positions with the maximum and the minimum noise index; a calculating unit which substitutes the maximum and minimum tube current values that can be provided by the present scan of the system into the existing tube current control model in the system to calculate the range of noise index of the position with the minimum noise index and the range of noise index of the position with the maximum noise index in the scanned area; a determining unit which determines if there is an intersection between the two ranges of noise index; and a control unit which performs control on the system based on the result of determination from the determining unit. If it is determined that there is an intersection between the two ranges of noise index, the central control unit controls the system to proceed with a subsequent scan according to a combination of the range of tube current value and the range of noise index that meets the requirement as selected by the user within the intersection; if it is determined that there is not an intersection between the two ranges of noise index, it means that the system does not meet the requirement for the area to be scanned and the central control unit controls the system to end the present scan.

In one embodiment, the central control unit includes a data combining unit which creates a combination in which the respective ranges of tube current value and the respective noise indexes that meet the requirement are of a relationship of one-to-one correspondence.

The number of said combinations is obtained by equally dividing the range of noise index in the intersection according to a value of the dosage adjustment range of the noise coefficient.

In the embodiments described herein, the correspondence relationship between the noise index and the range of tube current value that meet the requirement is displayed in a graph.

In one embodiment, the graph is a graph of a combination of the ranges of tube current value corresponding to the respective ranges of noise index that meet the requirement, and the horizontal axis thereof is the noise index and the longitudinal axis thereof is the range of tube current value. In such an embodiment, the graph is a histogram.

In another embodiment, the graph is a graph of a combination of the maximum and minimum tube current values corresponding to the respective noise indexes that meet the requirement, and the horizontal axis thereof is the maximum tube current value and the longitudinal axis thereof is the minimum tube current value. Said graph is a block diagram. Said minimum tube current value is less than or equal to the maximum tube current value.

The user operation interface includes a tube current control interface, and said graph and the tube current control interface are in the same user operation interface. When an operator clicks on any position on the graph, the user operation interface will automatically pop up the value of the range of noise index and the range of tube current value of the combination represented by said position.

An automatic filling relationship is established between said graph and tube current control interface. When the operator clicks on any position on the graph, the value of the range of noise index and the range of tube current value of the combination represented by said position will be automatically filled into the box for the range of tube current value and the box for the noise index in the tube current control interface. The noise value can be adjusted within the range of noise index.

The maximum and minimum tube current value that can be provided by the system are determined through the information of the present scout scan image, and technical parameters of the present scout scan including the voltage value and the thickness.

In another aspect, the embodiments described herein describe performing analysis processing during the scout scan of the subject so as to obtain the range of noise index of the position with the minimum noise index and the range of noise index of the position with the maximum noise index in the length of the area to be scanned, and determine whether there is an intersection between the two ranges of noise index so as to determine whether the system meets the requirement for scanning the subject to be scanned. The method, scanning detection device, and system of the present invention can effectively determine whether the system is in a condition that meets the requirements both for the range of tube current value and for the noise index with respect to the scanned subject, thus preventing the doctor from scanning the patient blindly by using the CT system without considering whether the system meets the requirement for scanning the patient owing to a lack of the method and device for detection and determination in the existing scanning system and preventing the patient from suffering unnecessary radiation. In addition, the present invention establishes a correspondence relationship between the range of current value and the noise index, thus enabling the doctor to select more accurately the condition required by the scanning so as to effectively reduce the radiation suffered by the scanned subject. Furthermore, the present invention establishes a relationship between the tube current control interface and the combination of the range of tube current value and the noise index that meets the requirement, thus enabling the values of the selected combination to be automatically filled into the corresponding box for the range of tube current value and prohibiting the user to enter and modify the range of current value, which facilitates the user's operation and reduces the mistakes that might be caused by the user's operation. The user can also adjust the noise coefficient within the range of noise adjustment so as to obtain better images.

DETAILED DESCRIPTION OF THE INVENTION

Embodiments of the invention are described in detail below with reference to the accompanying figures, but the invention is not limited to such embodiments.

When the X-ray CT apparatus scans a subject, it performs a scout scan first to obtain the length of the area to be scanned, then conducts analysis according to the tube current control model and sets input values of current and noise index to perform a subsequent scan. The present invention makes some improvement to the existing X-ray CT apparatus and the scanning method thereof.

Figure 7:
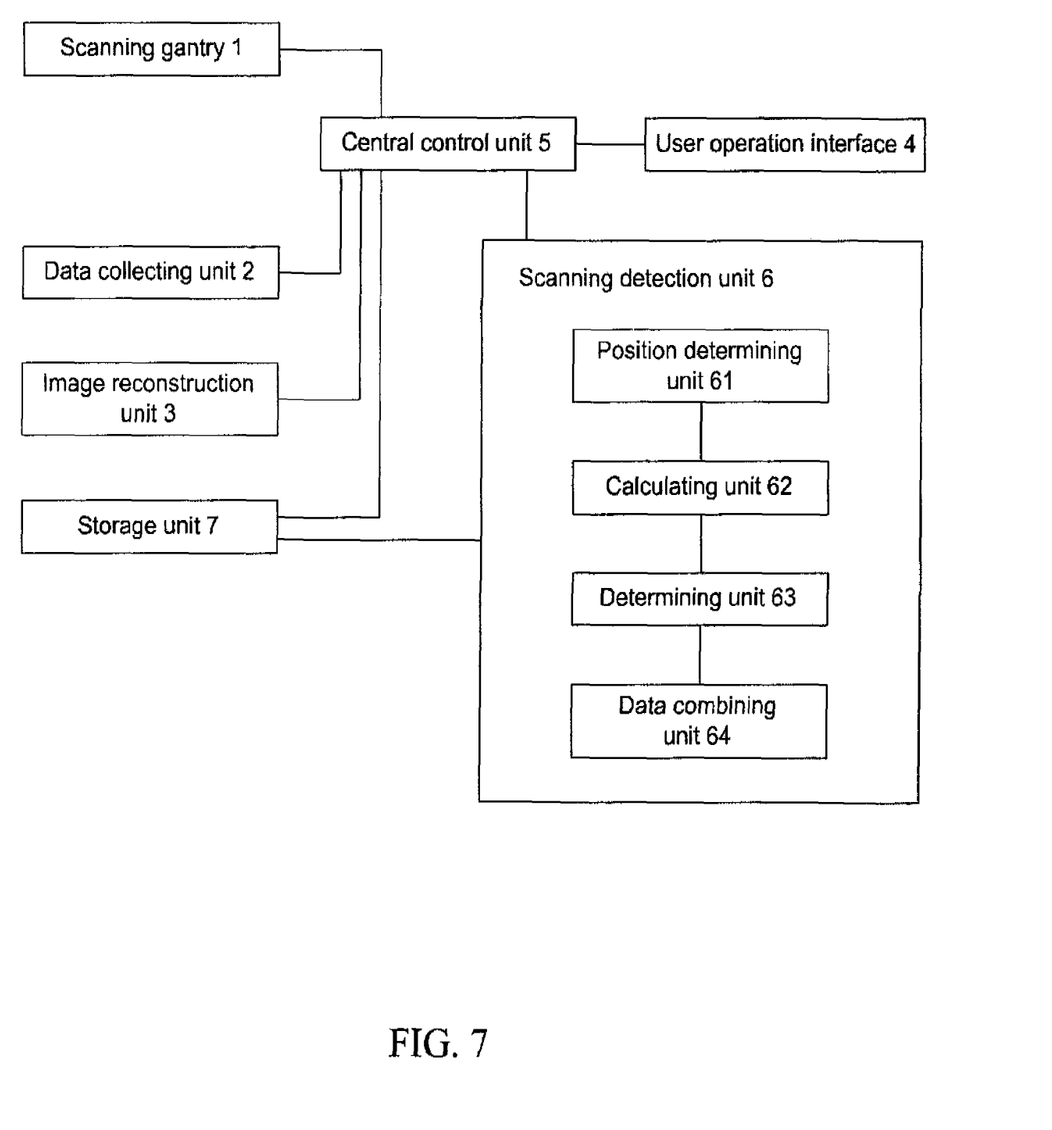
FIG. 7 is the functional block diagram of an X-ray CT system.

FIG. 7 is a block diagram of an X-ray CT system with a tube current control model according to the present invention. Said system is an embodiment of the present invention. An embodiment of the device of the present invention is illustrated by the structure of said system.

The X-ray CT system with a tube current control model according to the present invention comprises a scanning gantry 1 for performing a radiation scan including scout scan on a subject, a data collecting unit 2 for collecting and A/D converting scan data including scout scan data output from the scanning gantry, an image reconstruction unit 3 for reconstructing image from the scan data including the scout scan data sent from the data collecting unit, and for storing the reconstructed scout scan image data in a storage unit 7; a user operation interface 4 for the user's operation, through which the user selects the length of the area to be scanned according to the scout scan data and the scout scan image; and a central control unit 5 connected to the output terminal of the image reconstruction unit 3 for controlling the scanning gantry 1, the data collecting unit 2 and the user operation interface 4, the central control unit 5 receives the operation instruction of selecting the length of the area to be scanned as sent from the user operation interface 4, selects the length of the area to be scanned in the scout scan image sent from the image reconstruction unit, and displays it in the user operation interface 4; and a scanning detection unit 6 for analyzing and processing the scout scan data of the system and for detecting whether the system has a combination of the noise index and the range of tube current value that fits with the length of the area to be scanned so as to ensure the safety of the scanning of the system.

The scanning detection unit 6 comprises a position determining unit 61, a calculating unit 62, a determining unit 63 and a data combining unit 64. The position determining unit 61 analyzes in the length of the area to be scanned by means of the existing tube current control model, calculates the noise index of each Z-direction position at a certain presumed fixed tube current value (e.g. assume that the tube current value is 100 mA, the noise index output at any one position to be scanned is calculated, and the curve of the noise index of each position to be scanned is analyzed to obtain the positions with the maximum and minimum noise indexes; in view of the monotonic relationship between the tube current and the noise index, there is no special restriction for the previously mentioned certain fixed tube current value) to find out the positions with the maximum and the minimum noise indexes. One skilled in the art can use other similar methods to achieve the method of "determining the positions with the maximum and the minimum noise indexes". For example, such positions can be found indirectly according to experience by analyzing the distribution of the projection values of a certain scanned position.

The calculating unit 62 substitutes the maximum and minimum values of the tube current that can be provided by the present scan of the system into the existing tube current control model in the system to calculate the range of noise index of the position with the minimum noise index and the range of noise index of the position with the maximum noise index in the scanned area. For example, the maximum and minimum values of the tube current that can be provided by the present scan is 300 mA and 10 mA. 10 and 300 are substituted into the existing tube current control model to analyze the result of said position with the maximum noise index, and then two noise indexes (N11, N12) are obtained, where N11<N12. And 10 and 300 are substituted into the existing tube current control model to analyze the result of said position with the minimum noise index, and then two noise indexes (N21, N22) are obtained, where N21<N22.

The determining unit 63 determines if there is an intersection between the two ranges of noise index. For example, it can be determined whether said two ranges (N11, N12) and (N21, N22) have an intersection simply by comparing the four numbers N11, N12, N21 and N22.

Accordingly, the central control unit 5 controls the system in response to the result of determination made by the determining unit 63. If the result of determination shows that there is an intersection, the central control unit 5 controls the system to proceed with a subsequent scan according to a combination of the range of tube current value and the range of noise index as the parameter for a subsequent scan, which combination meets the requirement and is selected by the user within the intersection. If the result of determination shows that there is not an intersection, it means that the system does not meet the requirement for the length of the area to be scanned and the central control unit 5 controls the system to end the present scan.

Figure 10:
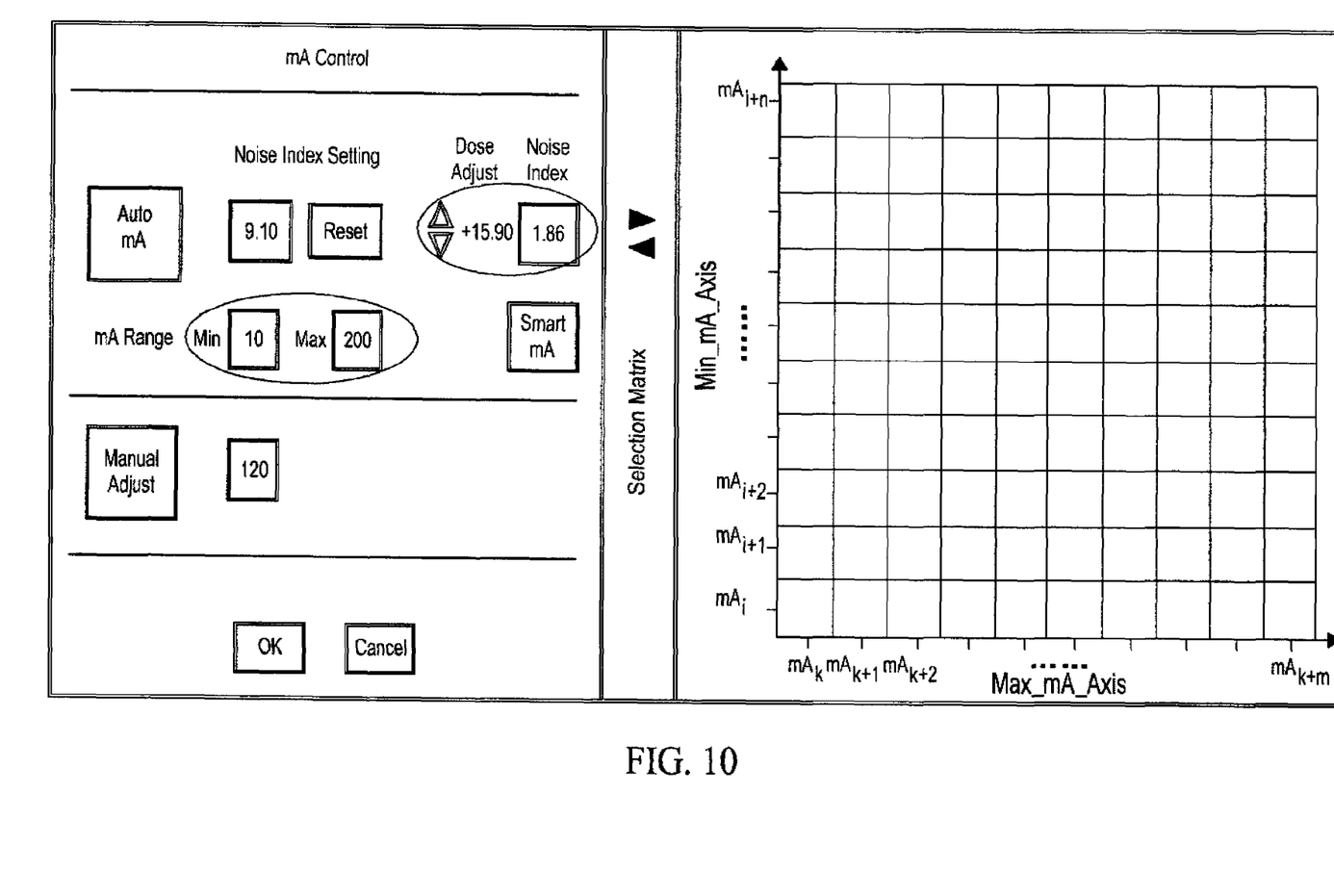
FIG. 10 is a schematic diagram showing a graph indicating that there is a combination of the range of tube current value and the range of noise index that meet the requirement, which graph is in the same display interlace as the tube current control interface.
Figure 11:
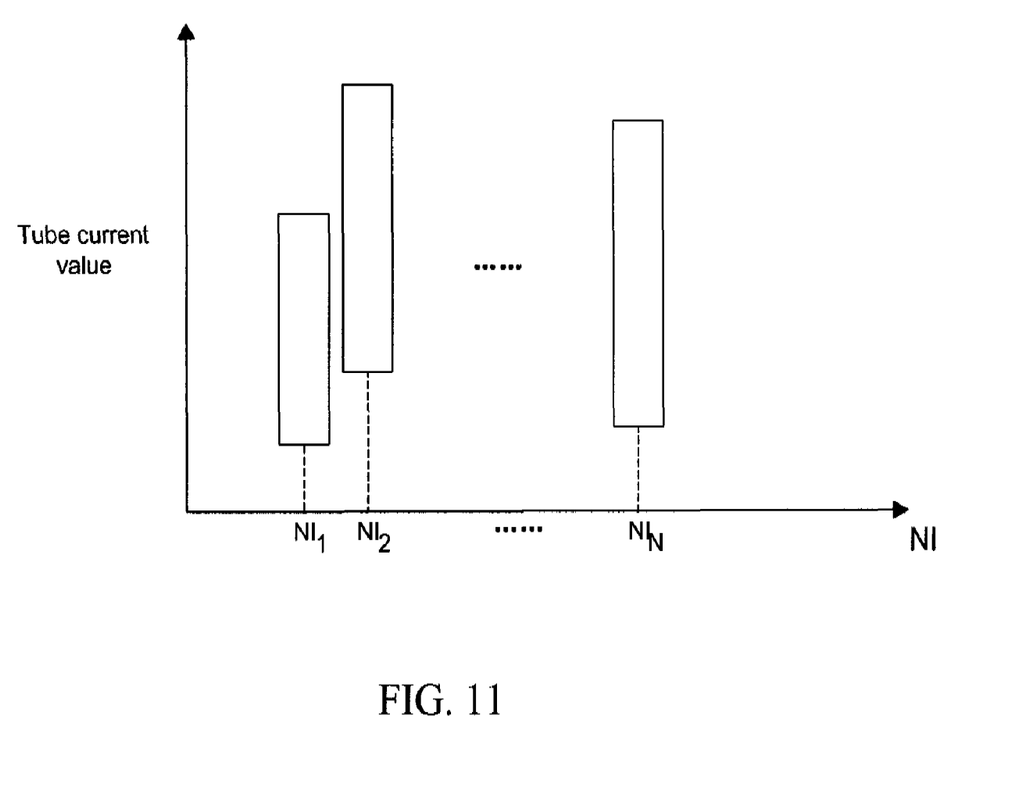
FIG. 11 is another schematic diagram showing a graph indicating that there is a combination of the range of tube current value and the range of noise index that meet the requirement.

When the determining unit 63 determines that there is an intersection, the central control unit 5 controls the data combining unit 64 to create a combination in which the noise index and the range of the tube current value that meet the requirement are of a one-to-one correspondence relationship. The created combination is displayed on the user operation interface 4 in a graph, as shown in FIGS. 10 and 11. The way of forming and displaying the graph will be described in detail in the method embodiment.

The user operation interface 4 includes a tube current control interface, and as shown in FIG. 10, said graph and the tube current control interface are in the same user operation interface. When the operator clicks on any position on the graph, the user operation interface will automatically pop up the value of the range of noise index and the range of tube current value of the combination represented by said position. An automatic filling relationship is established between said graph and tube current control interface. When the operator clicks on any position on the graph, the value of the range of noise index and the range of tube current value of the combination represented by said position will be automatically filled into the box for the range of tube current value and the box for the noise index in the tube current control interface. The user can adjust the noise value within the noise index range.

The maximum and minimum tube current values that can be provided by the system are determined and designed by the CT manufacturer through the information of the present scout scan image and the technical parameters of the present scout scan including the voltage value, thickness, different types of machines etc.

Figure 8:
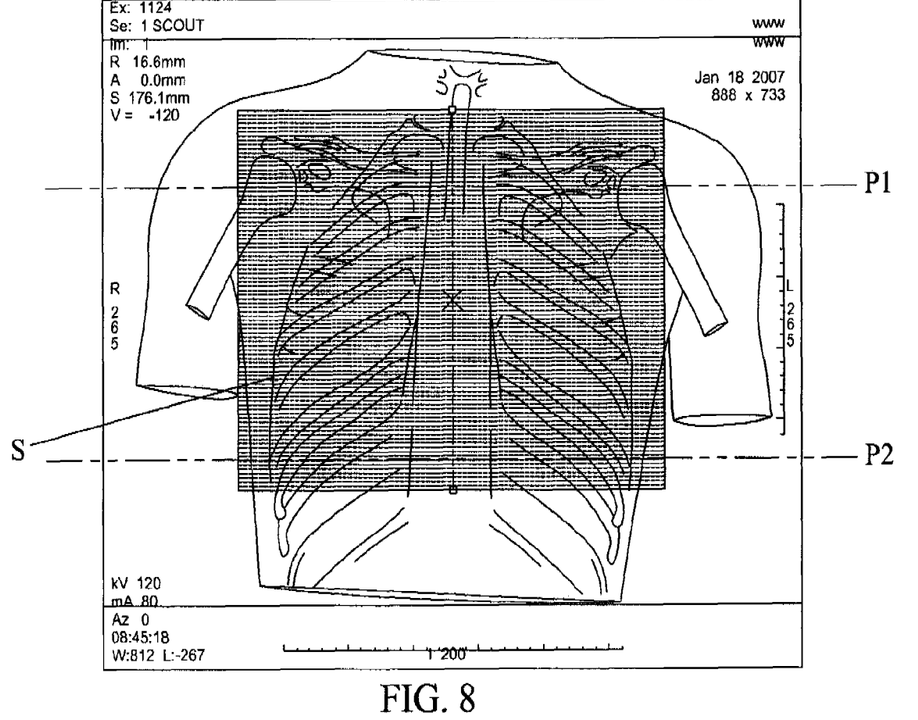
FIG. 8 is a scout scan image obtained using the X-ray CT system shown in FIG. 7.
Figure 12:
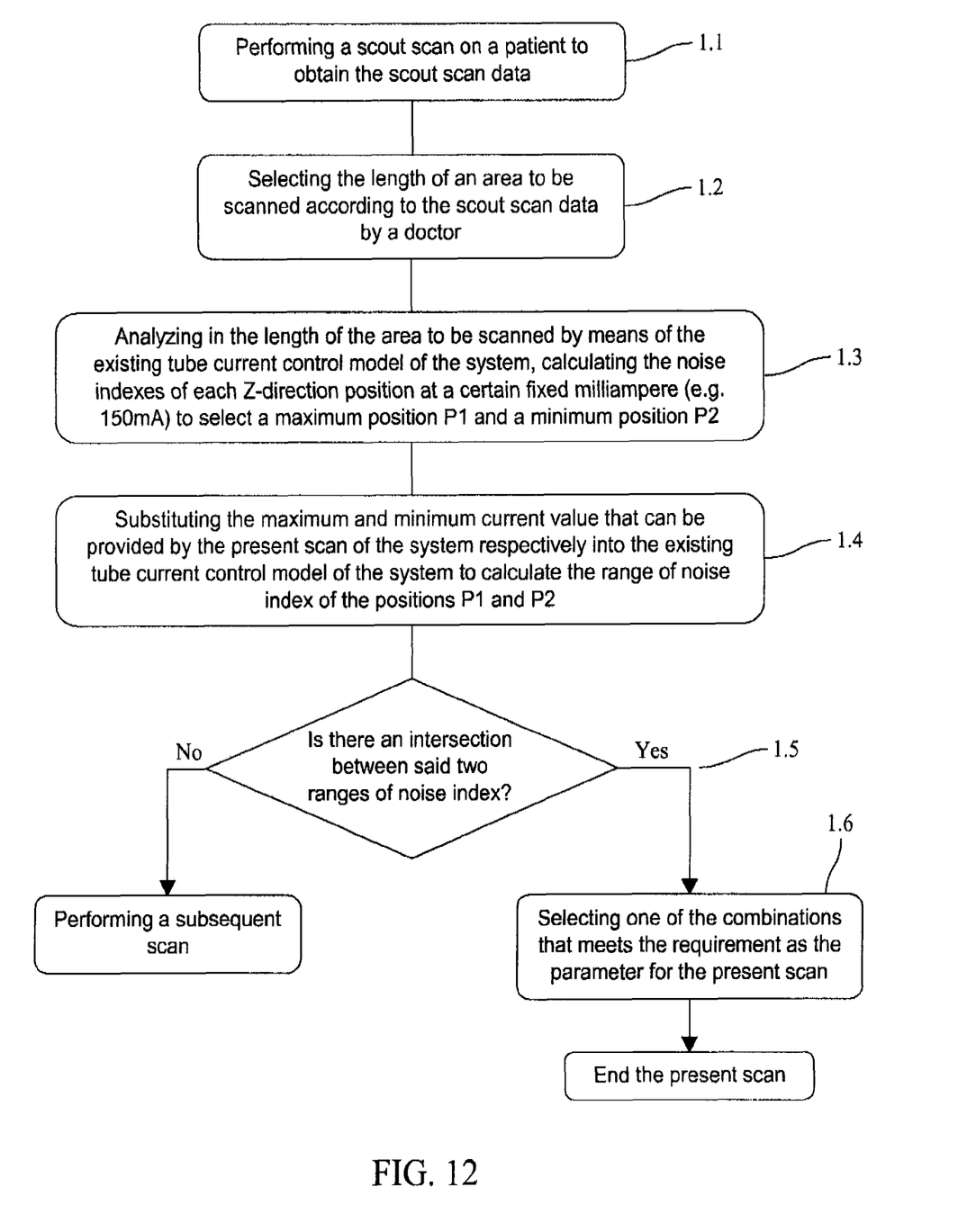
FIG. 12 is a illustrating an exemplary method of operating the X-ray CT system shown in FIG. 7.

FIG. 12 shows an embodiment of the scanning method of the X-ray CT apparatus. The method includes performing a scout scan on a subject to obtain the scout scan data (1.1), and selecting the length of the area to be scanned according to the scout scan data (1.2). For example, the length S of the area to be scanned that is determined by the existing method is as shown in FIG. 8. The method also includes automatically analyzing in the length of the area to be scanned by means of the tube current control model, and calculating the noise index of each Z-direction position at a certain fixed tube current value to find out the first position with the minimum noise index value and the second position with the maximum noise index value (1.3). For example, the first position P1 with the minimum noise index value and the second position P2 with the maximum noise index value are shown in FIG. 8, said first position P1 and second position P2 being inside the length S. Of course, one skilled in the art can also manually designate such positions interactively according to the information of the scout scan and his own experience. Moreover, the method includes substituting the maximum and minimum tube current values that can be provided by the present scan of the system respectively into the tube current control model of the system to perform calculation on the first position P1 with minimum noise index in the scanned area and the second position P2 with the maximum noise index in the scanned area, thus obtaining the range of noise index of the first position P1 and the range of noise index of the second position P2 respectively (1.4), and determining if there is an intersection between said two ranges of noise index (1.5). If there is, it means that there is a combination of the range of current value and the range of noise index that meets the requirement in the system, then a combination of the range of tube current value and the range of noise index is selected that meets the requirement within the intersection as the parameter for the present scan, and then proceed with a subsequent scan (1.6). If there is not, it means that the system does not meet the requirement for the length of the area to be scanned and the present scan is ended.

Figure 9:
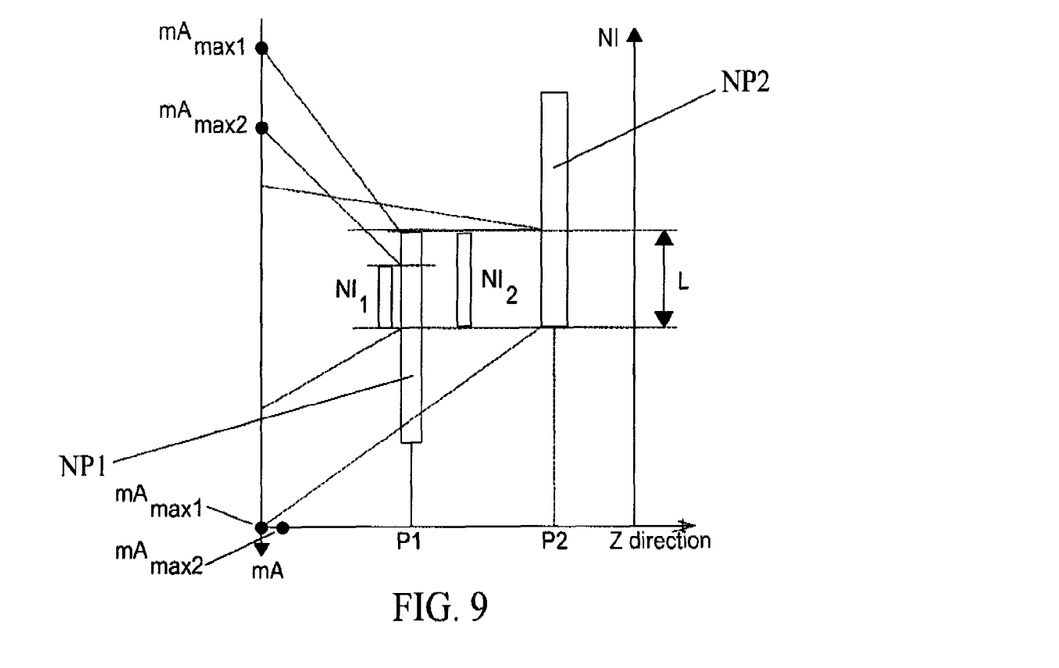
FIG. 9 is a schematic diagram showing a comparison between the ranges of noise index of the positions with the minimum noise index and with the maximum noise index within the length of the area to be scanned as obtained by means of the apparatus and method of the present invention.

FIG. 9 shows schematically that there is an intersection L between the noise index ranges NP1 and NP2 at the first position P1 and the second position P2 respectively. The horizontal axis represents the Z direction of the length of the area to be scanned, and the longitudinal axis represents the tube current values corresponding to the respective noise indexes. The intersection L as shown in the figure represents that within the range of tube current value [Min_mA, Max_mA] as given by the system, the system can output an image having consistent noise indexes when scanning the length S of the area to be scanned in the Z direction.

In one embodiment, selecting a combination of the range of tube current value and the range of noise index includes creating a combination wherein the respective range of tube current and the respective noise index that meet the requirement are of a one-to-one correspondence relationship. The present invention displays in a graph the correspondence relationship between the range of tube current and the noise index that meet the requirement.

FIG. 10 is a schematic diagram showing a combination wherein the respective range of tube current and the respective noise index that meet the requirement are of a one-to-one correspondence relationship according to the present invention. FIG. 10 is a graph of a combination of the maximum tube current value and the minimum tube current value corresponding to the respective noise indexes that meet the requirement, the horizontal axis thereof representing the maximum tube current value, and the longitudinal axis representing the minimum tube current value. Each possible range of current value in said combination is a current value array automatically generated by the system on the basis of the current value provided by the technical parameters of the present scan including voltage, thickness etc. Said array comprises discrete current values that meet the requirement, while the range of current value that does not meet the requirement is not shown in FIG. 10. The graph in this embodiment is a block diagram. Of course, the graph in this embodiment can also show the array formed of all the ranges of current value, and different colors are used to discriminate the blocks that represent the combinations meeting the requirement from the blocks that represent the combinations which do not meet the requirement, for example, the range represented by green blocks meeting the requirement, while the range represented by yellow blocks not meeting the requirement.

FIG. 11 a schematic diagram of another embodiment of the combination wherein the respective range of tube current value and the respective noise index that meet the requirement are of a one-to-one correspondence relationship according to the present invention. The graph shown in FIG. 11 is a graph of a combination of the ranges of tube current value corresponding to the respective ranges of noise index that meet the requirement, and the horizontal axis thereof represents the noise index, the longitudinal axis represents the range of tube current value. In this embodiment, the number of said combinations is obtained by equally dividing the range of noise index within the intersection according to the value of the dosage adjustment range of the noise coefficient provided by the system. For example, the dosage adjustment range of the noise coefficient provided by the system is ±0.5, i.e. the value of the range is 1, if the range of noise index in the intersection is 1 mA to 11 mA, then ten equally divided ranges of the noise index can be obtained, i.e. 1-2, 2-3, . . . , 10-11, each range of noise index forming a combination with the corresponding maximum and minimum tube current values. The histogram is used in this embodiment to represent the relationship among the combinations. Of course, the number of the combinations may also be obtained by non-equally dividing the range of noise index in the intersection according to the value of the dosage adjustment range of the noise coefficient provided by the system as required by the design.

According to logical relationship, in the range of current value in each combination that meets the requirement, the minimum value is equal or less than the maximum value.

The maximum and minimum tube current value that can be provided by the system in the method of the present invention are determined through the information of the present scout scan image, the technical parameters of the scans (e.g. axial scan, helical scan, etc.) that are to be performed after the present scout scan, including the voltage value and the thickness.

In the method of the present invention, when the user selects a combination of the range of tube current value and the range of noise index that meets the requirement, the maximum and minimum values in the range of tube current value in the combination are automatically filled into the box for the range of tube current value in the tube current control interface of the system, and the corresponding noise indexes are also filled into the box for the noise index in the tube current control interface of the system. For example, when the user clicks on a block in FIG. 10 or a column in FIG. 11, the range of noise index and the value of the range of current value corresponding to said block or column are popped up automatically. Accordingly, these values are automatically filled into the boxes for the minimum, maximum values of the range of tube current value and for the noise index in the tube current control interface that is in the same display interface as the graph. Of course, the user can also manually enter values into the corresponding boxes according to the values popped up on the interface. But when the values entered by the user are not consistent with those popped up on the interface, the system will refuse the wrongly entered values. In this embodiment, the user cannot enter and modify the value of the range of tube current value, but he can adjust the noise coefficient within the corresponding range of noise index.

The position determining unit 61, calculating unit 62, determining unit 63 and data combining unit 64 of the present invention can be integrated into the central control unit 5, or they can be solidified into the central control unit 5 through the corresponding solidify software so as to achieve the respective functions of the position determining unit 61, the calculating unit 62, the determining unit 63 and the data combining unit 64.

The apparatus having a corresponding solidified software provided in the central control unit 5 thereof and the operation method thereof according to the present invention are specifically illustrated below by the example of scanning the upper part of the body of a patient.

The patient is sent to the scanning gantry 1, and the user operation interface is operated to input the scout scan instruction to perform a scout scan on the patient. The central control unit 5 receives the instruction sent from the user operation interface 4 and controls the scanning gantry 1 to perform a scout scan on the upper part of the body of the patient. The data collecting unit 2 receives the information of the scout scan sent from the scanning gantry 1 and sends said information to the image reconstruction unit 3. The image reconstruction unit 3 reconstructs an image from said information of the scout scan to obtain a scout scan image of the upper part of the body of the patient and sends the information of said scout scan image to the central control unit 5 and the storage unit 7 to be stored. The central control unit 5 controls the display unit of the user operation interface 4 to display the image of the upper part of the body, and as shown in FIG. 8, the doctor selects the length S of the area to be scanned according to said scout scan image of the upper part of the body.

When the doctor sends the instruction of selecting the length of the area to be scanned by operating on the user operation interface 4, the central control unit 5 receives said instruction and processes the scout scan image so as to display it on the display unit. The doctor presses the button of the tube current in the user operation interface 5 to activate the automatic tube current control interface. Meanwhile, the central control unit 5 runs the solidified software for determining position, automatically analyzes in the length S of the area to be scanned by means of the tube current control model, and calculates the noise indexes of each Z-direction position at a current value of 150 mA to find out the first position P1 with the minimum noise index value and the second position P2 with the maximum noise index value, as shown in FIG. 8. After running the solidified software for determining position, the central control unit 5 runs the solidified software for calculation. The central control unit obtains from elsewhere or stores in itself the maximum and minimum values of the current that can be provided by the present scan of the system, and substitutes said maximum and minimum values of the current into the tube current control model of the system to conduct calculation on the first position P1 and the second position P2, thus obtaining the range of noise index of the first position P1 and the range of noise index of the second position P2, as shown in FIG. 9. Subsequently, the central control unit 5 runs the solidified software for determination and determines if there is an intersection between the two ranges of noise index obtained by running the solidified software for calculation, and the central control unit 5 controls the operation of the scan of the system based on the result of determination. When the result of determination is no, that is, when there is no intersection, it means that the system does not have a combination of the range of tube current value and the noise index that meets the requirement for scanning the length of the area to be scanned of the patient, and the central control unit 5 controls the system to end the present scan. When the result of determination is yes, that is, when there is an intersection, it means that the system has a combination of the range of tube current value and the noise index that meets the requirement for scanning the length of the area to be scanned of the patient, and the central control unit 5 executes the solidified software for data combination to segment the noise indexes in the intersection, and to establish and display on the display unit in the manner of blocks the correspondence between the range of noise index of each segment and the corresponding range of tube current value, as shown in FIG. 10. When the central control unit 5 runs said solidified softwares, the mechanical part of the system is in a stationary state.

The doctor presses the automatic tube current button on the tube current control interface and clicks on any one of the dark colored blocks in the block diagram that is on the same display unit as the tube current control interface, then the respective boxes for the range of tube current value and the noise coefficient in the tube current control interface are automatically filled with the range of tube current value and the noise index value represented by the clicked block. The doctor can adjust the noise coefficient to obtain better images. Then the doctor only has to press the "Confirm" button in the tube current control interface and the "Confirm" button in the user operation interface to complete the procedure of the present scan.

With the apparatus and method of the present invention, the user could learn whether in the system there is a combination of the range of tube current value and the range of noise index that meets the requirement for the length of the area to be scanned with respect to different scans; besides, when the system has a combination that meets the requirement, it can calculate automatically to obtain the combination and display it on the display interface in a graph. The user only needs to click on any position on the graph, then the system can perform a subsequent scan. Of course, the user can also adjust the noise index.

What is claimed is:

1. A method of operating an X-ray CT apparatus, said method comprising:

performing a scout scan on a subject to obtain scout scan data;

selecting a length of an area to be scanned according to the scout scan data;

analyzing the length of the area to be scanned to determine a position having a maximum noise index value and a position having a minimum noise index value;

substituting a maximum tube current value and a minimum tube current value that can be provided by a present scan of the X-ray CT apparatus into a tube current control model of the X-ray CT apparatus to calculate a first range of noise index corresponding to the position with minimum noise index and a second range of noise index corresponding to the position with the maximum noise index;

determining if an intersection exists between the first range of noise index and the second range of noise index;

if such an intersection does not exist, ending the present scan of the X-ray CT apparatus; and if such an intersection exists, selecting a combination of a range of tube current value and a third range of noise index within the intersection to perform a subsequent scan.

2. The method of operating an X-ray CT apparatus according to claim 1, wherein selecting a combination comprises creating a combination such that the range of tube current value and the third range of noise index are of a one-to-one correspondence relationship.

3. The method of operating an X-ray CT apparatus according to claim 1, wherein analyzing the length of the area to be scanned comprises using the tube current control model to automatically analyze the length of the area to be scanned and to calculate a noise index for each Z-direction position at a certain fixed tube current value to determine the position with the maximum noise index value and the position with the minimum noise index value.

4. The method of operating an X-ray CT apparatus according to claim 1, wherein selecting a combination comprises selecting the combination from a plurality of combinations obtained by one of equally dividing and dividing according to a preset requirement the range of noise index in the intersection according to a value of a dosage adjustment range of a noise coefficient.

5. The method of operating an X-ray CT apparatus according to claim 1, further comprising the maximum tube current value and the minimum tube current value that can be provided by the system based on the information of the scout scan image and technical parameters of the scout scan including a voltage value and a thickness.

6. The method of operating an X-ray CT apparatus according to claim 1, wherein selecting a combination comprises:

automatically filling the maximum value and minimum value in the range of tube current value in the combination into a box for the range of tube current value in a tube current control interface of X-ray CT apparatus; and filling the corresponding noise indexes into a box for the noise index in the tube current control interface.

7. A scanning detection device for use with an X-ray CT system having a tube current control model, wherein the X-ray CT system includes a scanning gantry configured to perform a radiation scan including a scout scan on a subject, a data processing unit for configured to collect and process the scout scan data output from the scanning gantry, an image reconstruction unit configured to reconstruct an image from the scout scan data sent from the data processing unit, a central control unit configured to control the X-ray CT system, and a user operation interface for a user to operate, wherein the user selects the length of an area to be scanned according to the scout scan data and the scout scan image, said scanning detection device comprises:

a position determining unit configured to determine a position with a certain noise index value and to analyze the length of the area to be scanned to determine a first position with a minimum noise index and a second position with a maximum noise index in a Z-direction of the length of the area to be scanned;

a unit configured to determine a range of tube current value of the X-ray CT system, and to determine a maximum tube current value and a minimum tube current value that can be provided by the present scan according to the scout scan data output from the scanning gantry and system technical parameters of the present scan;

a calculating unit configured to substitute the maximum tube current value and the minimum tube current value that can be provided by the X-ray CT system currently into a tube current control model to calculate a first range of noise index corresponding to the first position and a second range of noise index corresponding to the second position; and a determining unit configured to determine if there is an intersection between the first range of noise index and the second range of noise index, and if such an intersection exists, to display a message via the user operation interface indicating that a subsequent scan is to be performed and a value of the range of noise index within the intersection and the corresponding maximum and minimum tube current values are used as the system parameters for the subsequent scan, and if no such intersection exists, to display a message via the user operation interface indicating ending the present scan.

8. The scanning detection device according to claim 7, further comprising a data combining unit configured to combine and divide the data including the range of tube current value and the range of noise index in the intersection to establish a relationship of one-to-one correspondence.

9. The scanning detection device according to claim 8, wherein the central control unit is configured to perform graphical processing on the correspondence relationship established by said data combining unit and to display the correspondence relationship on the user operation interface in a graph.

10. The scanning detection device according to claim 9, wherein the graph is a combination of the maximum tube current value and the minimum tube current value corresponding to the respective noise indexes that meet the requirement, and a horizontal axis of the graph being the maximum tube current value and a longitudinal axis of the graph being the minimum tube current value.

11. The scanning detection device according to claim 8, wherein a number of data combinations is obtained by equally dividing the range of noise index in the intersection according to a value of a dosage adjustment range of a noise coefficient provided by the X-ray CT system.

12. The scanning detection device according to claim 9, wherein the user operation interface includes a tube current control interface, the graph and the tube current control interface being in the same user operation interface, and wherein when an operator clicks on any position on the graph, the user operation interface automatically displays the range of tube current value and a value of the range of noise index of the combination represented by the clicked position.

13. An X-ray CT system having a tube current control model for processing scan data, said system comprising:
a scanning gantry configured to perform a radiation scan including a scout scan on a subject;
a data collecting unit configured to collect and to convert from analog to digital the scan data including the scout scan data output from said scanning gantry;
an image reconstruction unit configured to reconstruct a scout scan image according to the scan data including the scout scan data sent from said data collecting unit, and to store data of the reconstructed scout scan image in a storage unit;
a user operation interface for a user to operate, through which the user selects the length of an area to be scanned according to the scout scan data and the scout scan image; and
a central control unit connected to said image reconstruction unit, said central control unit configured to:
control said scanning gantry, said data collecting unit, and said user operation interface;
receive an operation instruction of selecting the length of the area to be scanned as sent from said user operation interface;
receive an operation instruction of selecting the length of the area of the scout scan image sent from said image reconstruction unit; and
display the scout scan image on said user operation interface, wherein said central control unit comprises:
a position determining unit configured to analyze the length of the area to be scanned to determine a position with a maximum noise index and a position with a minimum noise index;
a calculating unit configured to substitute the maximum tube current value and the minimum tube current value that can be provided by a present scan into the tube current control model to calculate a range of noise index of the position with the minimum noise index and a range of noise index of the position with the maximum noise index; and
a determining unit configured to determine if an intersection exists between the two ranges of noise index;
said central control unit configured to control said system based on a result of determination from the determining unit, wherein if such an intersection exists, said central control unit controls said system to proceed with a subsequent scan according to a combination of the range of tube current value and the range of noise index that meets the requirement as selected by the user within the intersection, and wherein if such an intersection does not exist, said central control unit controls said system to end the present scan.

14. The X-ray CT system according to claim 13, wherein said central control unit further comprises a data combining unit configured to create a combination in which the range of tube current value and noise index that meet the requirement are of a relationship of one-to-one correspondence.

15. The X-ray CT system according to claim 13, wherein a number of combinations is obtained by equally dividing the range of noise index in the intersection according to a value of a dosage adjustment range of a noise coefficient.

16. The X-ray CT system according to claim 14, wherein the correspondence relationship between the range of tube current value and the noise index that meet the requirement is displayed by a graph.

17. The X-ray CT system according to claim 16, wherein the graph is a combination of the ranges of tube current value corresponding to the respective noise index ranges that meet the requirement, a horizontal axis of the graph being the noise index and a longitudinal axis of the graph being the range of tube current value.

18. The X-ray CT system according to claim 14, wherein said user operation interface includes a tube current control interface, the graph and said tube current control interface are in the same user operation interface, and wherein when an operator clicks on any position on the graph, said user operation interface automatically displays the range of tube current value and the value of the range of noise index of the combination represented by the clicked position.

19. The X-ray CT system according to claim 18, wherein an automatic filling relationship is established between the graph and said tube current control interface, such that when the operator clicks on any position on the graph, the range of tube current value and the value of the range of noise index of the combination represented by the clicked position will be automatically filled into a box for the range of tube current value and a box for the noise coefficient in said tube current control interface.

20. The X-ray CT system according to claim 13, wherein the maximum tube current value and the minimum tube current value that can be provided by said system are determined through information of the present scout scan image, and technical parameters of the present scout scan including a voltage value and a thickness, and said position determining unit is configured to analyze the length of the area to be scanned by means of the tube current control model and to calculate a noise index of each Z-direction position at a certain fixed tube current value to find out each Z-direction position.

* * * * *